United States Patent
Aubert

(10) Patent No.: US 7,354,550 B2
(45) Date of Patent: Apr. 8, 2008

(54) DISINFECTION OR STERILISATION METHOD

(75) Inventor: Bruno Aubert, Connaux (FR)

(73) Assignee: NV Bekaert SA, Zwevegem (BE)

( * ) Notice: Subject to any disclaimer, the term of this patent is extended or adjusted under 35 U.S.C. 154(b) by 505 days.

(21) Appl. No.: 10/380,005

(22) PCT Filed: Sep. 6, 2001

(86) PCT No.: PCT/EP01/10310

§ 371 (c)(1),
(2), (4) Date: Apr. 11, 2003

(87) PCT Pub. No.: WO02/20065

PCT Pub. Date: Mar. 14, 2002

(65) Prior Publication Data

US 2003/0170157 A1    Sep. 11, 2003

(30) Foreign Application Priority Data

Sep. 11, 2000    (FR) .................................. 00 11622

(51) Int. Cl.
*A61L 2/00* (2006.01)
(52) U.S. Cl. ................ 422/1; 422/4; 422/129; 422/292; 100/90; 100/229 A; 100/240; 100/179
(58) Field of Classification Search ................ 422/26, 422/1, 4, 129, 939, 198, 292; 100/90, 240, 100/229 A, 179
See application file for complete search history.

(56) References Cited

U.S. PATENT DOCUMENTS

| 4,552,720 A | 11/1985 | Baker, Sr. et al. |
| 5,401,444 A | 3/1995 | Spinello |
| 2003/0177907 A1 | 9/2003 | Aubert |

FOREIGN PATENT DOCUMENTS

| CA | 2 246 364 | 8/1997 |
| EP | 0 796 625 A2 | 9/1997 |
| FR | 2 767 700 A1 | 3/1999 |
| FR | 2 779 350 A1 | 12/1999 |
| WO | WO 99/11299 A1 | 3/1999 |
| WO | WO 99/64076 A1 | 12/1999 |

OTHER PUBLICATIONS

Patent Abstracts of Japan, vol. 1999, No. 09, Jul. 30, 1999, JP 11-104655.

*Primary Examiner*—Gladys J P Corcoran
*Assistant Examiner*—Sean E. Conley
(74) *Attorney, Agent, or Firm*—Foley & Lardner LLP

(57) ABSTRACT

The invention relates to a disinfection or sterilisation method. The material to be disinfected is introduced in a receptacle and the receptacle is sealed. Subsequently, the sealed receptacle is heated under a water vapour and/or radical pressure. The water vapour pressure and/or radical pressure is obtained during the heating by evaporating the water and the radicals absorbed and/or formed in a natural way at the surface of the material.

10 Claims, 2 Drawing Sheets

DISINFECTION OR STERILISATION METHOD

FIELD OF THE INVENTION

The invention relates to a method to disinfect and sterilize material. The method is in particular suitable to disinfect and sterilize medical waste. The invention further relates to a device for carrying out this method.

BACKGROUND OF THE INVENTION

Several methods to disinfect material are presently known in the art. Examples of such methods are methods based on chemical disinfection, radiation disinfection, thermal disinfection or thermal destruction. However, these methods show several drawbacks.

Chemical disinfection or sterilisation is a method that reaches its limits very rapidly, because the germs become more and more resistant and because it is often impossible to guarantee a good penetration of the disinfecting agent in the material to be disinfected (e.g. needles obstructed by blood, . . . ).

Disinfection or sterilisation by radiation is known to treat material such as medical waste.

However, this is an expensive technique requiring high investment costs.

Thermal disinfection or sterilisation is known as a very efficient technique to treat for example scalpels and other surgical instruments, but it does not allow to treat other materials such as medical waste with the same efficiency.

Thermal destruction is for example performed in an incinerator or furnace. This technique necessitates very large and expensive installations to respect the emission standards, and more particularly the dioxin emission standards. Moreover, this technique destroys and does not treat.

Today, the disinfection of metal surfaces as for example the surface of instruments is largely dominated by the treatment in humid heat (autoclaves) and many industrials have tried in vain to apply it to other fields, such as e.g. to medical waste.

For the disinfection of surgical instruments good results have been obtained. It has been shown that the reduction of the contamination can be reduced well over 6 Log by disinfecting surgical instruments in an autoclave.

For the disinfection of other materials such as cotton, a much lower disinfection level is actually obtained.

Indeed, in-depth disinfection of corpuses made of cellulose, glass or stainless steel fibers, such as medical waste, necessitates that all possible efforts have to be made to guarantee that the heat and the vapour reach all parts.

In most cases, this is realised by shredding and mixing together the waste in an autoclave.

However, the large variety of the materials that are susceptible to be contaminated and so the differences of specific thermal and heat conductivity lead to divergent thermal transfers. Metals will for example be heated more rapidly by the water vapour condensation than cellulose.

Therefore, it has been tried to apply an additional heating such as microwaves or high frequency heating, but the waste also presents a large diversity of dielectric properties leading to heterogeneous thermal transfers.

Indeed, several autoclave procedures have tried to prove their efficiency in experimental procedures to disinfect material infected by germs, but the fact that there exists a high heterogeneity in material does not guarantee a homogeneous treatment of the entire waste.

SUMMARY OF THE INVENTION

It is an object of the present invention to provide a method of disinfecting and sterilising material that avoids the drawbacks of the prior art.

It is another object to provide a method to disinfect material with high efficiency at low costs.

It is a further object to provide a device for carrying out a method to disinfect material, in particular medical waste.

According to a first aspect of the present invention a disinfection or sterilisation method is provided.

The method comprises the steps of providing a receptacle holding a material to be disinfected. The receptacle has a possibly contaminated internal surface $S_c$. The surface $S_c$ can be considered as the part of the internal surface which possibly had been in contact with the material to be disinfected, for example when the material is introduced in the receptacle.

The receptacle is further provided with means to seal the receptacle in an airtight way. When sealed the receptacle has an internal surface $S_i$ which is equal or larger than the surface $S_c$;

sealing said receptacle in an airtight way;

heating said sealed receptacle whereby said surface $S_i$ and said material are heated under a water vapour and/or radical pressure.

The water vapour pressure and/or radical pressure is obtained during the heating by evaporating the water and the radicals absorbed and/or formed in a natural way at the surface of the material to be disinfected and/or at the surface $S_i$.

The water vapour and/or radical pressure is preferably higher than 1 bar, for example 2 bar or 3.4 bar.

The radicals are preferably hydroxyl (OH) radicals. OH radicals are known as very reactive free radicals and as strong oxidants which may kill diverse microorganisms and degrade diverse volatile organic compounds.

Possibly, the radicals comprise also CO radicals.

The material to be disinfected may comprise any kind of material that can be introduced in the receptacle. Examples of material comprise medical waste, surgical instruments or food packaging.

The material to be disinfected may also be part of the receptacle itself. It may for example comprise the internal surface or part of the internal surface of the receptacle.

Since both the material and the surface $S_i$ are heated under a water vapour and/or radical pressure, both are treated and disinfected in the same way.

Disinfecting the internal surface of the receptacle is important to avoid possible recontamination of the disinfected material after the treatment or to avoid contamination of material introduced in the receptacle.

In a preferred method the water and radical pressure is obtained by eliminating, before the heating, all or substantially all the air and the free space in and around the material to be disinfected in order to allow the water and the radicals absorbed and/or formed in a natural way at the surface of the material to be sufficiently numerous to obtain a saturated water vapour pressure or a substantially saturated water vapour pressure during the heating of the material.

With substantially saturated water vapour pressure is meant a pressure that is at least 90% of the saturated water vapour pressure.

A saturated water vapour pressure is preferred. However, in practice it is difficult to reach this. It has been shown by the present invention that a good disinfection and sterilisation could be obtained in a substantially saturated water vapour pressure.

The following example further clarifies the terms saturated and substantially saturated water vapour pressure.

When an autoclave with a volume of air $V_a$ at a temperature of 25° C. the air is heated to a temperature of 134° C., the pressure $P_a$ of the volume $V_a$ is:

$$P_a = \frac{(273+134)}{(273+25)} * 1 = 1.37 \text{ bar}.$$

A vacuum of 0.2 bar, before the heating, permits to decrease this volume of air up to one fifth of the volume $V_a$.

This means that the pressure of this reduced volume of air will be 1,37/5=0.27 bar.

At 134° C., the pressure of a saturated water vapour is normally 3 bar.

Consequently, the water pressure in the volume $V_a$ will be $P_s$=3−0.27=2.73 bar. This is about 90% (2.73/3) of the saturated water vapour pressure and is considered as a substantially saturated water vapour pressure.

It is known, that all materials in atmospheric conditions absorb a small quantity of water on their surface and that this water presents itself partly under a radical form due to the interaction with the material.

In order to guarantee that the water and the radicals, such as OH, at the surface of the material and/or in the pores of material when the material comprises fibrous or granular material, are systematically present under the form of vapour, it is preferred that the air and free space in and around the material to be disinfected or sterilised is substantially eliminated.

With eliminating substantially all the air and free space in and around the material is meant an elimination of the air and the free space so that a saturated or substantially saturated water vapour and/or radical pressure is obtained. In practice this means that the volume of air and free space in and around the material to be disinfected is less than 20% and preferably less than 10% of the total volume of the material. More preferably, the volume of air and free space in and around the material is less than 5%, for example less than 2% of the total volume of the material.

By the elimination or substantial elimination of the air and free space in and around the material to be disinfected, the water and the OH radicals absorbed or naturally formed at the surface or in the porous structure of the material will, when they are completely or partly evaporated through the heating process at temperatures over 100° C., finally be highly concentrated in the very small remaining volume and the vapour or radicals and germs will very probably meet.

The action of such a radical-charged water vapour is extremely efficient to destroy germs.

The elimination or substantial elimination of the air and free space in and around the material to be disinfected can be achieved in a number of different ways.

A first way to realize the elimination of the air and free space in and around the material is by reducing the volume of the receptacle comprising the material and/or by compacting said material to be disinfected.

Alternatively, the elimination of the air and free space in and around the material can be achieved by injecting a material, such as a liquid into the receptacle. Examples of suitable material to be injected into the receptacle are oils, such as mineral oil and silicones.

Preferably, the air in and around the material is evacuated through a filter medium. More preferably, the air in and around the material is evacuated through a filter medium comprising metal fibers.

A filter medium comprising metal fibers shows a high filter efficiency. Furthermore, a filter medium comprising metal fibers is characterised by a high specific surface so that a high quantity of water and radicals can be absorbed. The water and radicals are not only adsorbed at the surface of the filter medium but also in the porous structure of the filter medium. Consequently, by using a filter medium comprising metal fibers the desired water vapour pressure and/or radical pressure is obtained more easily.

The receptacle is closed in an airtight way, for example by closing a valve.

It is preferred that the pressure inside the receptacle is slightly decreased, for example by increasing the volume of the receptacle slightly before the heating step.

By this small decrease in pressure, a vapour pressure such as a saturated or substantially saturated vapour pressure is obtained more easily during the subsequent heating.

The material to be disinfected and the surface $S_i$ of the receptacle are heated to a temperature over 100° C. Preferably, the temperature is between 100 and 250° C., and more preferably between 134 and 150° C., for example 138° C.

The heating can be realised by any method known in the art and may comprise for example heating by means of one or more electrical resistors, a fluid exchanger, a high frequency heater or by a combination thereof.

In the method according to the present invention, the water and the radicals, such as OH radicals, absorbed and/or formed in a natural way at the surfaces of the material to be disinfected are sufficient to guarantee a disinfection under pressure of saturated water vapour as the air and the residual volume around the aforementioned surfaces have been reduced to the minimum.

Materials made of metal absorb water and radicals easily.

Consequently, such materials can easily be disinfected.

However, it has been shown that the procedure according to the present invention can also be used for the disinfection of other materials.

Dry cotton for example still contains several grams of water per kg.

After compression and disinfection at 90% of the cotton, there only remains 0.1 liter of air per kg of cotton.

Knowing that at 145° C., the pressure of saturated water vapour amounts to 4.2 bar, it is necessary to have 0.1/22.4*18/4.2*(273+145)/273=0.03 g of water to obtain the saturated vapour pressure.

So, even dry cotton contains a few grams of water and could be disinfected under good conditions. Moreover, the absorbed water partly presents itself under a radical form of the OH type. OH radicals are known as extremely aggressive radicals and allow it to destroy the proteinic structures and so the germs easily.

In autoclaves, these OH radicals cannot react with the same efficiency as the volume around the material to be disinfected is too large to have a sufficient probability that the radical will meet the germ.

At present, autoclaves can be successfully used for the sterilisation of surgical instruments. In the light of the present invention, this can be explained since the surgical instruments comprise metallic surfaces on which the germs to be destroyed are located and metallic surfaces absorb the water vapour and the radicals more easily.

When materials with a low heating capacity or low insulation, such as cotton are disinfected in an autoclave, the problems are much greater.

In this case, the water vapour or the radicals have very little chance to meet the material to be disinfected since the material is placed in a large metallic volume that will preferably condense the vapours.

This is further emphasised by the fact that the materials are often massive materials, such as a large bandage, as a result of which the water or the radicals have difficulties to penetrate into the material.

In the present invention the residual volume after the elimination or substantial elimination of the air and the free space is on the contrary very small and the probability of interaction is thus very large. This may be an explanation why the results obtained with the device according to the present invention are exceptional and can reach 13 Log, which is a million times better than the results obtained with the autoclaves.

The aforementioned procedure is appropriated for the disinfection and sterilisation of all kinds of materials. It can be used to disinfect as well dielectric or electric material, dry or humid material. Examples of materials to be disinfected are cotton, metal and plastics.

The procedure is in particular suitable to disinfect medical waste. It can also be used to disinfect surgical instruments, washbasins or floors.

Furthermore, the method can be adapted to disinfect garbage such as food packaging or plastics for example on board of ships.

According to a second aspect of the present invention a device for carrying out a method to disinfect material is provided.

The device comprises a receptacle holding a material to be disinfected.

The receptacle has a possibly contaminated internal surface $S_c$. The receptacle is provided with means to eliminate the air and free space in and around said material and with means to seal the receptacle in an airtight way.

When sealed, the receptacle has an internal surface $S_i$ which is equal or larger than the internal surface $S_c$.

The receptacle is further provided with means to heat the material and the surface $S_i$ of the receptacle under a saturated or substantially saturated water vapour and/or radical pressure.

The device comprises a receptacle comprising the material to be disinfected. This receptacle may be deformable or non-deformable.

The material to be disinfected may comprise any material that can be introduced in the receptacle, such as medical waste, surgical instruments or food packaging.

Alternatively, the material to be disinfected may be part of the receptacle in which the disinfection process is carried out. It may for example comprise the internal surface or part of the internal surface of the receptacle.

The receptacle is provided with means to seal the receptacle in an airtight way and with means to eliminate the air in and around the material to be disinfected.

The means to eliminate the air comprise for example means to reduce the volume of the receptacle and/or means to compress the material to be disinfected.

These means may for example comprise a piston which can be activated by means of a piston rod.

The air in and around the material to be disinfected can also be eliminated by closing the receptacle by means of an object that fits well in the cavity of the receptacle and/or that encloses the material to be disinfected well.

Another way to eliminate the air and free space in and around the material to be disinfected is by injecting a material such as an oil or a silicone into the receptacle.

The means to heat the material to be disinfected allow to heat the material to be disinfected and the surface $S_i$ of the receptacle to a temperature higher than 100° C.

Preferably, the material is heated to a temperature between 100 and 250° C., and more preferably to a temperature between 134 and 150° C., for example 138° C.

The heating can be realised in any way known to a person skilled in the art. The means for heating comprise for example at least one electrical resistor, a fluid exchanger, a high frequency heater or a combination thereof.

The heating can be indirect heating, for example by heating the receptacle that subsequently heats the medical waste.

Also a direct heating of the medical waste is possible. Indirect heating can for example be realised by means of electrical resistors that are installed at the external surface of the receptacle, by means of a heat exchange circuit comprising a heat conductive liquid that is installed at the external surface surface of the receptacle or by circulating electrical streams inside the receptacle if it is a metal receptacle.

Direct heating can for example be realised by the circulation of electrical streams if the material is made of metal. The electrical streams can be generated by electrical conduction, induction or capacity. Alternatively, direct heating can be realised by applying an electromagnetic field (microwaves or high frequencies) if the material to be disinfected shows dielectric losses.

Also the means to reduce the volume of the receptacle and/or the means to compress the material, such as a piston, can be provided with means to heat the material to be disinfected.

The time of the heat treatment is preferably between 1 and 60 minutes. It is clear that the time of the heat treatment is depending upon the temperature. A preferred heat treatment comprises a heating at 138° C. during 20 minutes.

Moreover, the treatment temperature depends on the desired type of disinfection and the nature of the infectious agents.

- In the event of non-pathogenetic agents, such as in food packaging, the temperature can only be maintained at 121° C. for 15 minutes.
- In the event of pathogenic agents, such as in waste or air filters of operation rooms, the temperature can be maintained at 138° C. for 20 minutes.
- For a very far-reaching disinfection and/or a disinfection over a short period, the temperature can be comprised between 1800 and 200° C. for one minute.

Preferably, the receptacle is further equipped with a filter medium and more preferably also with a valve.

The filter medium may filter the gases released during the compacting of the material to be disinfected.

The filter medium preferably comprises a sintered, nonwoven metal fiber web.

Metal fibers used for the filter medium according to the invention may be made of a conventional metal or metal alloy.

Preferred alloys are stainless steel such as stainless steel 316L, Hastelloy®, Inconel®, Nichrome®, Alloy HR.

The fibers of the filter medium preferably have a diameter ranging between 1 and 22 µm. More preferably, the metal fibers have a diameter between 1 and 10 µm, for example 2 µm or 5 µm.

A sintered, non-woven metal fiber web as filter medium is characterised by a low pressure drop and a high filter efficiency.

Furthermore, the filter medium has a high specific surface (about 600 m² for 1 m² of filter). Because of this high specific surface a high quantity of water and radicals can be absorbed and the desired water vapour pressure and/or radical pressure is obtained more easily.

A sintered, non-woven metal fiber web has a low thickness and consequently a low volume.

This has as result that the air and free space in and around the material to be disinfected can be eliminated to a higher degree.

BRIEF DESCRIPTION OF THE DRAWINGS

The invention will now be described into more detail with reference to the accompanying drawings wherein.

DESCRIPTION OF THE PREFERRED EMBODIMENTS OF THE INVENTION

Figure 1A:
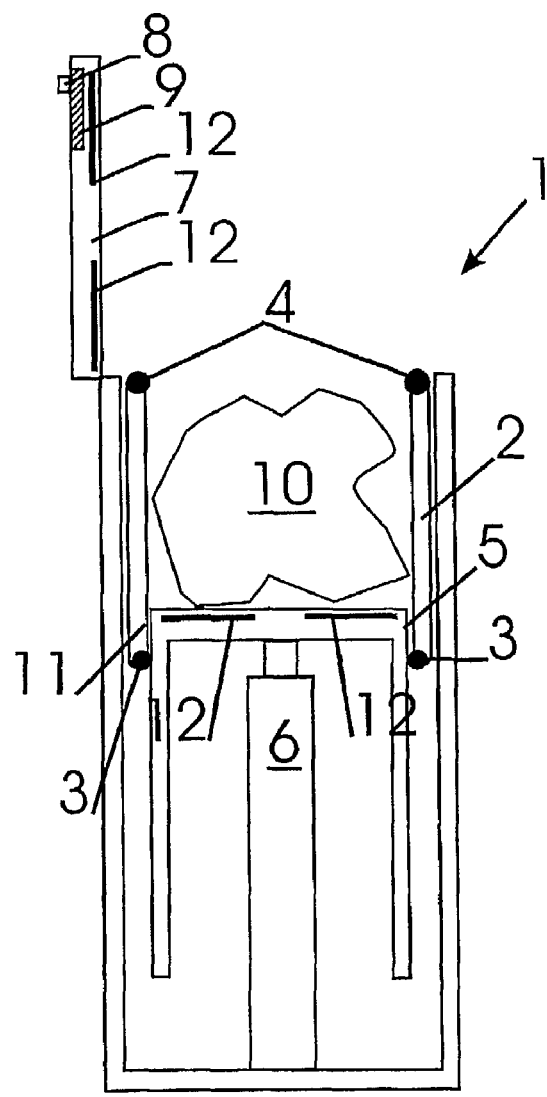
FIGS. 1a, 1b and 1c show a device to disinfect material according to the present invention and illustrates the process of disinfecting.
Figure 1B:
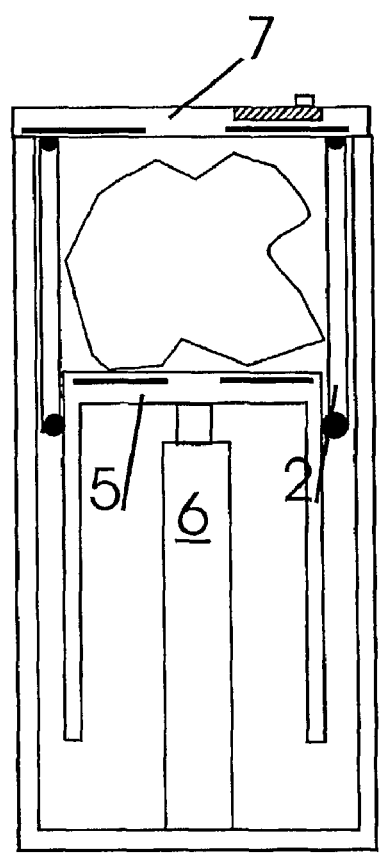
Figure 1C:
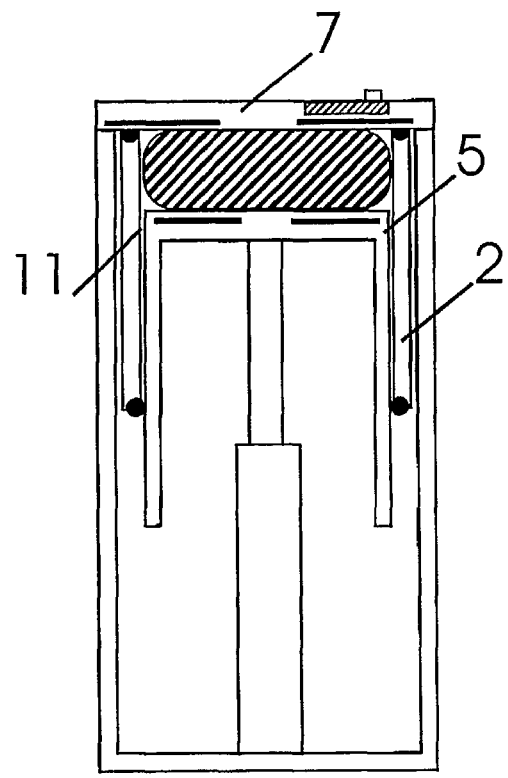

A disinfection method using a device according to the present invention is explained in more detail referring to FIGS. 1a, 1b and 1c. The method is in particular suitable to disinfect medical waste.

FIG. 1a shows schematically a device according to the present invention in open position, ready to receive material to be disinfected.

FIG. 1b shows the device in closed position during the compression (volume reduction). FIG. 1c shows the device during the heating step.

The device comprises a receptacle 2 in which the material to be disinfected can be introduced. The receptacle can for example be cylindrical, although also receptacles with other shapes can be considered.

The receptacle is equipped with gaskets 3, 12 at both ends on the internal circumference of the receptacle. These gaskets assure that the receptacle can be closed in an airtight way.

The receptacle is further provided with a piston 5. The piston preferably has a diameter adapted to the diameter of the receptacle to leave an intermediate volume between the receptacle and the piston which is quasi zero. The length of the piston is preferably longer than the length of the receptacle to assure that the gaskets 3 are always active.

By the presence of the gaskets the receptacle can be closed in an airtight way during the whole process, whatever the position of the piston is. In this way the internal surface of the receptacle is in the same conditions as the material to be disinfected. This means that not only the material to be disinfected but also the internal surface of the receptacle will be disinfected.

The piston 5 is equipped with electrical resistors or a heat conductive circuit (not represented) and can be moved by translation by means of a piston rod 6.

The receptacle can be closed by means of a lid 7.

The lid 7 is equipped with electrical resistors or a heat conductive circuit (not represented), a filter medium 9, a valve 8 and a liquid detector (not represented).

The filter medium is preferably a sintered non-woven metal fiber web comprising stainless steel fibers having a diameter of for example 2 µm. The filter medium has a thickness of 2 mm.

The valve 8 is located downstream the filter 9, in relation to the treatment room in such a way that when the valve 8 is closed, the filter 9 is placed under the same humid heat conditions necessary for the disinfection.

A preferred method to disinfect medical waste is described below in detail. The method comprises the following steps:

retracting the piston 5 to provide sufficient space to introduce the waste material (FIG. 1a). Preferably, the piston is retracted without being completely outside the receptacle 2.

introducing the medical waste 10 in the receptacle 2. Preferably, the medical waste is collected in a bag, for example in a polymer bag before being introduced in the receptacle.

A preferred bag comprises a composite polymer and comprises for example polyethylene at the inside of the bag and polyamide at its outside.

The polyethylene at the inside of the bag ensures a good adhesion with the medical waste and ensures that the medical waste maintains its form once it is compressed.

The polyamide at the outside of the bag avoids a strong adhesion between the bag and the inside of the receptacle.

By introducing contaminated material, the internal surface of the receptacle is possibly contaminated. In principle, the whole internal surface of the receptacle that had been in contact with the introduced material can be contaminated. This possibly contaminated surface is called $S_c$. As can be seen on FIG. 1a, this surface $S_c$ is determined by the position of the piston 5 when the material is introduced. The surface $S_c$ comprises the lateral sides of the receptacle from the top till the position of the piston and the surface of the piston 5.

closing the lid 7 to close the receptacle 2.

activating the piston 5 by means of the piston rod 6 to compress the waste.

If the materials to be disinfected are not very dense, as is the case for medical waste, the compression pressure shall be higher than 1 bar and shall preferably amount between 10 and 20 bars for an optimal disinfection and to allow the evacuation of almost all air and free space.

The valve 8 of the lid 7 remains open to allow the elimination of the air through the filter medium 9 (FIG. 1b).

It has to be noticed that the efforts of the piston rod 6 are immediately taken over by the lid 7 through the piston rod 6 and through the locking system of the lid. This allows to obtain a more efficient bi-axial type of compression (receptacle 2 is floating).

once the compression pressure is reached, maintaining the pressure during a time period which is for example between 1 second and 2 minutes. Preferably, this time period is longer than 10 seconds to allow the air to escape completely and to allow the materials to better keep their compressed state (FIG. 1c).

sealing the receptacle in an airtight way. This is achieved by closing the valve and by the presence of the gaskets 3 and 12 which are active during the whole process.

The internal surface of the receptacle once sealed, $S_i$, is thereby equal or larger than the possibly contaminated internal surface $S_c$.

As can be seen on FIG. 1c; the surface $S_i$ comprises the lateral sides of the receptacle from the top till the gaskets 3 and the surface of the piston 5. Also the lateral surfaces of the piston can be considered as comprised in the surface $S_i$.

preferably, the method further comprises the step of putting the piston 5 a few millimeters backwards to lower the pressure on the waste 10 and to create a vacuum that will allow to even more easily reach the saturated vapour pressure during the heating procedure.

This step is preferred since as the pressure cannot be measured in the treatment zone because of the mechanical tension to which it is exposed it must be measured on the compression piston rod 6. If the piston should remain on the waste, it would on the one hand not be possible to measure on the piston rod's 5 hydraulic circuit the pressure exercised by the water vapour at 145° C. On the other hand, the dilatation of the solid matters and even the liquids in the waste would considerably increase the pressure making it even more difficult to measure the pressure exercised only by the water vapour.

In the event liquids are present in the material to be disinfected (these liquids can be detected by a liquid detector, such as e.g. an electrode), the backward motion of the piston could even be slightly more important since the liquids' dilatation coefficients are larger than the solids' dilatation coefficients.

heating the piston 5 and the lid 7 to heat the material to be disinfected by the means for heating 12.

when the treatment temperature is reached, i.e. between 121° C. and 200° C., but preferably 145° C., the temperature is maintained a certain period of time to allow all waste to reach the same temperature (preferably this time period is between 15 and 120 minutes, and preferably at least 45 minutes for a compression at 10 bar and a compressed waste thickness of 10 cm).

During this heating step, not only the waste introduced in the receptacle, but also the internal surface of the receptacle $S_i$ is disinfected.

It can be seen on FIG. 1c that the surfaces 10 of the piston 4 and especially the surfaces of the receptacle 2, opposed to the treatment zone, are in the same conditions of confined space and disinfection by the water and the radicals that are in a natural way absorbed or formed on the surfaces of the waste and even on the surfaces of the receptacle 2 and the piston 4 thanks to the gaskets 3.

after the treatment, a cooling-down to 60° C. will allow to evacuate the waste in a completely safe way.

opening the lid 7 and activating the piston 6 to push the formed flat object of disinfected material outside.

removing the disinfected material from the receptacle.

Figure 2A:
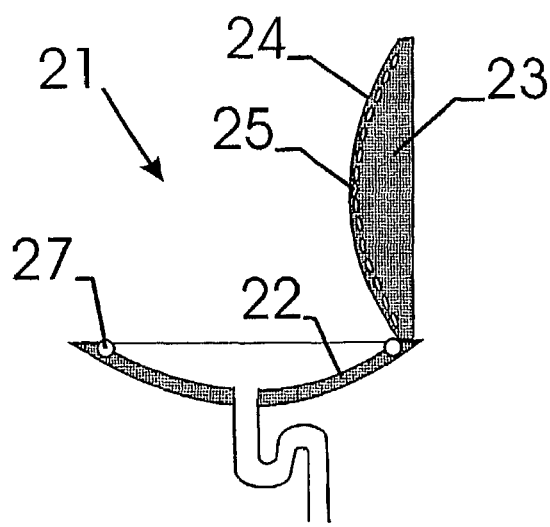
FIGS. 2a and 2b show the disinfection of a washbasin.
Figure 2B:
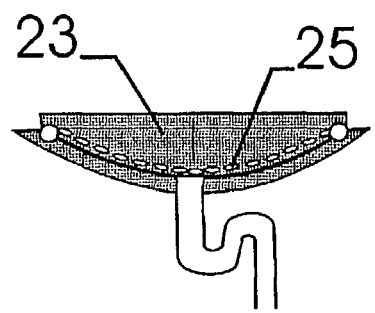

FIG. 2 illustrates a method to disinfect a washbasin. FIG. 2a shows the washbasin in open position; FIG. 2b shows the washbasin during the disinfection process.

The washbasin 21 having an internal surface 22 is provided with a lid 23.

The lid 23 is provided with means to heat 25. Furthermore the washbasin is provided with gaskets 27.

The internal surface 22 of the washbasin is possibly contaminated and should be disinfected.

In a first step, the washbasin is closed by placing the lid inside the cavity of the washbasin.

Preferably, the lid fits as perfectly as possibly in the cavity of the washbasin. In this way the free space created between the surface of the lid 24 and the internal surface of the washbasin 22 is as small as possible.

To disinfect the internal surface 22 of the washbasin 21, the lid is closed and the air is eliminated from the space between the lid and the internal surface of the washbasin. The gaskets assure that the washbasin is closed in an airtight way and facilitate the creation of a water vapour pressure and/radical pressure.

Subsequently, the internal surface 22 of the washbasin 21 is heated by the means for heating 25. The above described method to disinfect washbasins has as important advantage to avoid problems of increasing resistance of germs as is the case when washbasins are disinfected chemically.

The invention claimed is:

1. A disinfection and/or sterilisation method of a material; said method comprises the steps of:
   providing a receptacle holding a material to be disinfected, said receptacle having an internal surface Sc, said receptacle being provided with a seal adapted to seal the receptacle in an airtight way; said receptacle, when sealed, having an internal surface Si, said internal surface Si being at least one of equal to or larger than the internal surface Sc;
   sealing said receptacle in an airtight way;
   heating said sealed receptacle such that said internal surface Si and said material to be disinfected are heated under a saturated or substantially saturated water vapour and/or radical pressure, said saturated or substantially saturated water vapour and/or radical pressure being obtained by:
   (i) eliminating, before said heating, substantially all air and free space in and around said material to be disinfected,
   (ii) decreasing ambient pressure inside said receptacle before said heating and after said sealing, and
   (iii) evaporating the water and/or radicals absorbed and/or formed in a natural way at the surface of said material to be disinfected and/or said internal surface Si.

2. A method according to claim 1, wherein said radicals comprise at least one of OH radicals and CO radicals.

3. A method according to claim 1, wherein a volume of said air and free space in and around said material to be disinfected after said elimination is less than 20% of the total volume of said material to be disinfected.

4. A method according to claim 1, wherein said material to be disinfected is introduced in said receptacle.

5. A method according to claim 4, wherein said material to be disinfected is collected in a bag before being introduced in said receptacle.

6. A method according to claim 5, wherein said bag comprises a composite polymer bag, wherein an inside of said polymer bag comprises polyethylene and an outside of said bag comprises polyamide.

7. A method according to claim 1, wherein elimination of the air and the free space in and around said material to be disinfected is obtained by injecting matter into said receptacle.

8. A method according to claim 1, wherein said material to be disinfected comprises medical waste.

9. A method according to claim 1, wherein said material to be disinfected comprises surgical instruments.

10. A method according to claim 1, wherein said material to be disinfected comprises the surface of a washbasin.

* * * * *

UNITED STATES PATENT AND TRADEMARK OFFICE
CERTIFICATE OF CORRECTION

PATENT NO. : 7,354,550 B2 Page 1 of 1
APPLICATION NO. : 10/380005
DATED : April 8, 2008
INVENTOR(S) : Aubert It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 505 days Delete the phrase "by 505 days" and insert -- by 593 days --

Signed and Sealed this

Twenty-eighth Day of July, 2009

JOHN DOLL
*Acting Director of the United States Patent and Trademark Office*